(12) United States Patent
Hölzemann et al.

(10) Patent No.: US 7,425,574 B2
(45) Date of Patent: Sep. 16, 2008

(54) BENZOFURAN OXYETHYLAMINES AS ANTIDEPRESSANTS AND ANXIOLYTICS

(75) Inventors: Günter Hölzemann, Seeheim-Jugenheim (DE); Kai Schiemann, Seeheim-Jugenheim (DE); Henning Böttcher, Darmstadt (DE); Timo Heinrich, Gross-Umstadt (DE); Christoph Seyfried, Seeheim-Jugenheim (DE); Joachim Leibrock, Pfungstadt (DE); Chrisoph Van Amsterdam, Darmstadt (DE); Gerd Bartoszyk, Weiterstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 484 days.

(21) Appl. No.: 10/546,029

(22) PCT Filed: Jan. 19, 2004

(86) PCT No.: PCT/EP2004/000348

§ 371 (c)(1),
(2), (4) Date: Aug. 18, 2005

(87) PCT Pub. No.: WO2004/074281

PCT Pub. Date: Sep. 2, 2004

(65) Prior Publication Data

US 2006/0084693 A1   Apr. 20, 2006

(30) Foreign Application Priority Data

Feb. 18, 2003   (DE) ................. 103 06 941

(51) Int. Cl.
*A61K 31/404* (2006.01)
*C07D 405/12* (2006.01)

(52) U.S. Cl. .................. 514/414; 548/452; 548/454; 514/412

(58) Field of Classification Search ................ 548/452, 548/454; 514/412, 414
See application file for complete search history.

(56) References Cited

U.S. PATENT DOCUMENTS

| 4,404,217 | A |   | 9/1983 | Demarne et al. |
| 5,436,264 | A |   | 7/1995 | Pfister et al. |
| 5,532,241 | A |   | 7/1996 | Bottcher et al. |
| 6,110,956 | A |   | 8/2000 | Mewshaw et al. |
| 6,121,307 | A | * | 9/2000 | Mewshaw et al. ........... 514/414 |
| 6,291,683 | B1 | * | 9/2001 | Mewshaw et al. ........... 548/452 |

FOREIGN PATENT DOCUMENTS

| EP | 0 648 767 | 4/1995 |
| WO | WO 99/51575 | 10/1999 |
| WO | WO 99/51576 | 10/1999 |
| WO | WO 02/083666 | 10/2002 |

* cited by examiner

*Primary Examiner*—Golam M Shameem
(74) *Attorney, Agent, or Firm*—Millen, White, Zelano & Branigan, P.C.

(57) ABSTRACT

Novel benzofuranoxyethylamines of the formula (I), in which $R^1$, $R^2$, $R^3$, $R^4$, m and n have the meanings indicated in Patent Claim (1), which have a strong affinity to the $5HT_{1A}$ receptors and/or $5HT_{1D}$ receptors. The compounds inhibit serotonin reuptake, exhibit serotonin-agonistic and -antagonistic properties and are suitable as antidepressants, anxiolytics, antipsychotics, neuroleptics and/or antihypertonics.

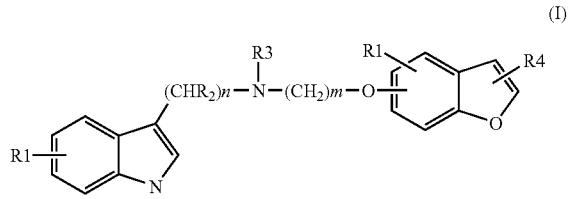

(I)

13 Claims, No Drawings

BENZOFURAN OXYETHYLAMINES AS ANTIDEPRESSANTS AND ANXIOLYTICS

The invention relates to benzofuranoxyethylamines of the formula I

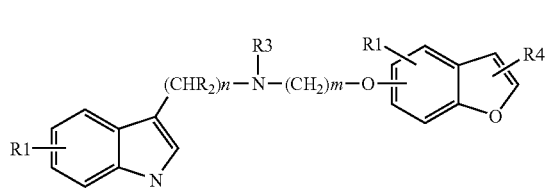

in which
R$^1$ denotes H, mono- or disubstitution by OH, OA, CN, Hal, COR or CH$_2$R
R denotes OH, OA, NH$_2$, NHA or NA$_2$
R$^2$, R$^3$ denote H or A
R$^4$ denotes H, mono- or disubstitution by OH, OA, NH$_2$, NHA, NA$_2$, CN, Hal, COR or CH$_2$R
A denotes alkyl having 1, 2, 3, 4, 5 or 6 atoms
Hal denotes F, Cl, Br or I
m denotes 2, 3, 4, 5 or 6
n denotes 1, 2, 3 or 4, and pharmaceutically usable derivatives, solvates and stereoisomers thereof, including mixtures thereof in all ratios.

The invention had the object of finding novel compounds having valuable properties, in particular those which are used for the preparation of medicaments.

Other indole derivatives are known from EP 648767 (Merck) or from WO 99/51575 (American Home Prod.).

It has been found that the compounds of the formula I according to the invention and physiologically acceptable acid-addition salts thereof, while being well tolerated, have valuable pharmacological properties since they have actions on the central nervous system, in particular 5-HT reuptake-inhibiting actions, in that they influence serotoninergic transmission. They have an affinity to the 5-HT$_x$ receptors, with subtype 5 HT$_{1A}$ being particularly preferred. In 5 HT$_x$, denotes 1A, 1D, 2A, 2C, 3 or 4.

Since the compounds also inhibit serotonin reuptake, they are particularly suitable as antidepressants and anxiolytics. The compounds exhibit sero-tonin-agonistic and -antagonistic properties. They inhibit the binding of tritiated serotonin ligands to hippocampal receptors (Cossery et al., European J. Pharmacol. 140 (1987), 143-155) and inhibit synaptosomal serotonin reuptake (Sherman et al., Life Sci. 23 (1978), 1863-1870).

Ex-vivo demonstration of serotonin reuptake inhibition is carried out using synaptosomal uptake inhibition (Wong et al., Neuropsychopharmacol. 8 (1993), 23-33) and p-chloro-amphetamine antagonism (Fuller et al., J. Pharmacol. Exp. Ther. 212 (1980), 115-119).

The binding properties of the compounds of the formula I can be determined, inter alia, by known 5-HT$_{1A}$ (serotonin) binding tests (5-HT$_{1A}$ (serotonin) binding test: Matzen et al., J. Med. Chem., 43, 1149-1157, (2000) in particular page 1156 with reference to Eur. J. Pharmacol.: 140, 143-155 (1987).

The compounds according to the invention can be employed for the treatment of diseases which are associated with the serotonin neurotransmitter system and in which, for example, high-affinity serotonin receptors (5-HT$_{1A}$ receptors) are involved.

The compounds of the formula I are therefore suitable both in veterinary and also in human medicine for the treatment of dysfunctions of the central nervous system and of inflammation. They can be used for the prophylaxis and combating of the consequences of cerebral infarction (apoplexia cerebri), such as strokes and cerebral ischaemia, and for the treatment of extra-pyramidal motor side effects of neuroleptics and of Parkinson's disease, for the acute and symptomatic therapy of Alzheimer's disease and for the treatment of amyotrophic lateral sclerosis. They are likewise suitable as therapeutic agents for the treatment of brain and spinal cord trauma. In particular, however, they are suitable as medicament active ingredients for anxiolytics, antidepressants, antipsychotics, neuroleptics, antihypertonics and/or for positively influencing obsessive-compulsive disorder (OCD), anxiety states, panic attacks, psychoses, anorexia, delusional obsessions, migraine, Alzheimer's disease, sleeping disorders, tardive dyskinesia, learning disorders, age-dependent memory impairment, eating disorders, such as bulimia, drugs misuse and/or sexual dysfunctions.

An important indication for the administration of the compound of the general formula I are psychoses of all types, in particular also mental illnesses from the schizophrenia group. In addition, the compounds can also be employed for reducing defects in cognitive ability, i.e. for improving learning ability and memory. The compounds of the general formula I are also suitable for combating the symptoms of Alzheimer's disease. In addition, the substances of the general formula I according to the invention are suitable for the prophylaxis and control of cerebral infarctions (apoplexia cerebri), such as cerebral strokes and cerebral ischaemia. The substances are furthermore suitable for the treatment of diseases such as pathological anxiety states, overexcitation, hyperactivity and attention disorders in children and youths, severe developmental disorders and disorders of social behaviour with mental retardation, depression, obsessive disorders in the narrower (OCD) and broader sense (OCSD) certain sexual dysfunctions, sleeping disorders and disorders in nutrient uptake, and psychiatric symptoms as part of age dementia and dementia of the Alzheimer's type, i.e. diseases of the central nervous system in the broadest sense.

The compounds of the formula I are likewise suitable for the treatment of extrapyramidal motor diseases, for the treatment of side effects which occur in the treatment of extrapyramidal motor diseases with conventional anti-Parkinson's medicaments, or for the treatment of extrapyramidal symptoms (EPS) induced by neuroleptics.

Extrapyramidal motor diseases are, for example, idiopathic Parkinson's disease, parkinsonian syndrome, dyskinetic choreatic or dystonic syndromes, tremor, Gilles de la Torette's syndrome, ballism, muscle cramps,. restless legs syndrome, Wilson's disease, Lewy bodies dementia, Huntington's and Tourette's syndrome.

The compounds according to the invention are also particularly suitable for the treatment of neurodegenerative diseases, such as, for example, lathyrism, Alzheimer's, Parkinson's, and Huntington's.

The compounds of the formula I are particularly suitable for the treatment of side effects which occur in the treatment of idiopathic Parkinson's disease with conventional Parkinson's medicaments. They can therefore also be used as add-on therapy in the treatment of Parkinson's disease. Known Parkinson's medicaments are drugs such as L-dopa (levodopa) and L-dopa combined with benserazide or carbidopa, dopamine agonists, such as bromocriptine, apomorphine, cabergoline, pramipexole, ropinirole, pergolide, dihydro-α-ergocriptine or lisuride, and all medicaments which effect stimulation of the dopamine receptor, inhibitors of catechol O-methyl transferase (COMT), such as entacapone or tolcapone, inhibitors of monoamine oxidase (MAO), such as selegiline, and antagonists of N-methyl D-aspartate (NMDA) receptors, such as amantadine or budipine.

The compounds of the general formula I and tolerated salts and solvates thereof can thus be employed as active ingredients for medicaments, such as anxiolytics, antidepressants, neuroleptics and/or antihypertonics.

A measure of the uptake of a medicament active ingredient in an organism is its bioavailability.

If the medicament active ingredient is supplied intravenously to the organism in the form of an injection solution, its absolute bioavailability, i.e. the fraction of the drug which reaches the systemic blood, i.e. the general circulation, in unchanged form, is 100%.

In the case of oral administration of a therapeutic active ingredient, the active ingredient is generally in the form of a solid in the formulation and must therefore first be dissolved so that it is able to overcome the entry barriers, for example the gastrointestinal tract, the oral mucous membrane, nasal membranes or the skin, in particular the stratum corneum, or can be absorbed by the body. Pharmacokinetic data, i.e. on the bioavailability, can be obtained analogously to the method of J. Shaffer et al, J. Pharm. Sciences, 1999, 88, 313-318.

A further measure of the absorbability of a therapeutic active ingredient is the logD value, since this value is a measure of the lipophilicity of a molecule.

If the compounds of the general formula I are optically active, the formula I covers both each isolated optical antipode and also the corresponding possibly racemic mixtures in any conceivable composition.

The term solvates of the compounds of the formula I is taken to mean adductions of inert solvent molecules onto the compounds of the formula I which form owing to their mutual attractive force. Solvates are, for example, mono- or dihydrates or addition compounds with alcohols, such as, for example, with methanol or ethanol.

The invention relates to the compounds of the formula I and salts and solvates thereof according to Claim 1 and to a process for the preparation of compounds of the formula I and salts, solvates and stereoisomers thereof, characterised in that a compound of the formula II

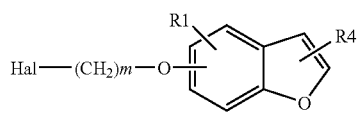

in which
$R^1$, $R^4$, Hal and m have the meanings indicated in claim 1 is reacted with a compound of the formula III

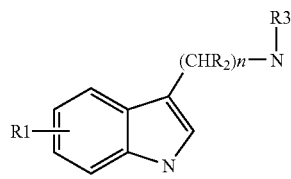

in which
$R^1$, $R^2$, $R^3$ and n
have the meanings indicated in claim 1, and/or
a basic or acidic compound of the formula I is converted into one of its salts or solvates by treatment with an acid or base.

The term pharmaceutically usable derivatives is taken to mean, for example, the salts of the compounds according to the invention and so-called prodrug compounds.

The term prodrug derivatives is taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as described, for example, in Int. J. Pharm. 115, 61-67 (1995).

A denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl, and is unbranched (linear) or branched. Particular preference is given to methyl or ethyl.

A also denotes cycloalkyl.

Cycloalkyl preferably denotes cyclopropyl, cyclobutyl, cyclopentyl, cyclohexyl or cycloheptyl.

Hal preferably denotes F, Cl, Br, but also I.

OA preferably denotes methoxy, ethoxy, propoxy, isopropoxy, butoxy or tert-butoxy.

R preferably denotes $NH_2$, OH, O-methyl or O-ethyl.

$R^1$ preferably denotes CN or F.

$R^2$ preferably denotes H or methyl.

$R^3$ preferably denotes H or methyl.

$R^4$ preferably denotes $CONH_2$, $COOC_2H_5$, CONHA.

m preferably denotes 2 or 3.

n preferably denotes 2 or 4.

Accordingly, the invention relates, in particular, to the compounds of the formula I in which at least one of the said radicals has one of the preferred meanings indicated above.

The compounds of the formula I according to Claim 1 and also the starting materials for the preparation thereof are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

If desired, the starting materials can also be formed in situ, so that they are not isolated from the reaction mixture, but instead are immediately converted further into the compounds of the formula I according to Claim 1.

The starting compounds of the formula II and III are generally known. If they are novel, however, they can be prepared by methods known per se.

Compounds of the formula I can be prepared by reaction of the compounds of the formula II with compounds of the formula III under standard conditions.

The reaction is generally carried out in an inert solvent, in the presence of an acid-binding agent, preferably an alkali or alkaline earth metal hydroxide, carbonate or bicarbonate, or another salt of a weak acid of the alkali or alkaline earth metals, preferably of potassium, sodium, calcium or caesium. The addition of an organic base, such as ethyldiisopropylamine, triethylamine, dimethylaniline, pyridine or quinoline, may also be favourable. The reaction time, depending on the conditions used, is between a few minutes and 14 days, the reaction temperature is between about 0° and 150°, normally between 20° and 130°.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, N-methylpyrrolidone, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane, at temperatures between 0 and 100°.

Free amino groups can furthermore be acylated in a conventional manner using an acid chloride or anhydride or alkylated using an unsubstituted or substituted alkyl halide or reacted with $CH_3$—C(=NH)—OEt, advantageously in an inert solvent, such as dichloromethane or THF, and/or in the presence of a base, such as triethylamine or pyridine, at temperatures between −60 and +30°.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic mono- or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, para-chlorophenoxyisobutyric acid, cyclohexanecarboxylic acid, glucose 1-phosphate, naphthalenemono- and disulfonic acids or laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline earth metal salts, or into the corresponding ammonium salts using bases (for example sodium hydroxide, potassium hydroxide, sodium carbonate or potassium carbonate).

The invention also relates to the compounds of the formula I according to Claim 1 and physiologically acceptable salts or solvates thereof as medicament active ingredients.

The invention furthermore relates to compounds of the formula I and physiologically acceptable salts or solvates thereof as $5HT_{1A}$, $5HT_{1D}$, $5HT_{2A}$ agonists and as inhibitors of 5HT reuptake.

The invention also relates to the compounds of the formula I according to Claim 1 and physiologically acceptable salts or solvates thereof for use in combating diseases.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

The invention furthermore relates to the use of the compounds of the formula I and/or physiologically acceptable salts thereof for the preparation of a medicament (pharmaceutical composition), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

The invention furthermore relates to the use of a compound of the general formula I and/or pharmaceutically usable derivatives, solvates and stereoisomers thereof, including mixtures thereof in all ratios, for the preparation of a medicament which is suitable for the treatment of human or animal diseases, in particular diseases of the central nervous system, such as pathological stress states, depression and/or psychoses, for reducing side effects in the treatment of high blood pressure (for example with alpha-methyldopa), for the treatment of endocrinological and/or gynaecological diseases, for example for the treatment of agromegaly, hypogonadism, secondary amenorrhoea, post-menstrual syndrome and undesired lactation in puberty and for the prophylaxis and therapy of cerebral diseases (for example migraine), in particular in geriatrics, in a similar manner to certain ergot alkaloids, and for the control and prophylaxis of cerebral infarction (apoplexia cerebri), such as cerebral strokes and cerebral ischaemia, for the treatment of extrapyramidal motor diseases, for the treatment of side effects which occur in the treatment of extrapyramidal motor diseases with conventional anti-Parkinson's medicaments, or for the treatment of extrapyramidal symptoms (EPS) induced by neuroleptics. In addition, the pharmaceutical compositions and medicaments which comprise a compound of the general formula I are suitable for improving cognitive ability and for the treatment of the symptoms of Alzheimer's disease.

In particular, medicaments of this type are suitable for the treatment of mental illnesses from the schizophrenia group and for combating psychotic anxiety states. For the purposes of the invention, the term treatment includes prophylaxis and therapy of human or animal diseases.

The invention furthermore relates to the use of compounds of the formula I and/or pharmaceutically usable derivatives, solvates and stereoisomers thereof, including mixtures thereof in all ratios, for the preparation of a medicament for combating diseases which are associated with the serotonin neurotransmitter system and in which high-affinity serotonin receptors (5-HT$_{1A}$ receptors) and/or 5HT$_{1D}$ receptors are involved.

The invention furthermore relates to the use of compounds of the formula I and/or pharmaceutically usable derivatives, solvates and stereoisomers thereof, including mixtures thereof in all ratios, for the preparation of a medicament as anxiolytic, antidepressant, neuroleptic and/or antihypertensive.

The substances of the general formula I are normally administered analogously to known, commercially available pharmaceutical compositions (for example of bromocriptine and dihydroergocornine), preferably in doses of between 0.2 and 500 mg, in particular of between 0.2 and 15 mg, per dosage unit. The daily dosage unit is between 0.001 and 10 mg per kg of body weight. Low doses (of between 0.2 and 1 mg per dosage unit, 0.001 to 0.005 mg per kg of body weight) are particularly suitable for pharmaceutical compositions for the treatment of migraine. A dose of between 10 and 50 mg per dosage unit is preferred for other indications. However, the dose to be administered depends on a multiplicity of factors, for example on the efficacy of the corresponding component, the age, the body weight and the general state of health of the patient.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may comprise, for example, separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Above and below, all temperatures are indicated in 0° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the product is purified by chromatography on silica gel, by preparative HPLC and/or by crystallisation. The purified compounds are optionally freeze-dried.

Mass spectrometry (MS): EI (electron impact ionisation) M$^+$

FAB (fast atom bombardment) (M+H)$^+$

ESI (electrospray ionisation) (M+H)$^+$ (unless stated otherwise)

EXAMPLE 1

Preparation of 7-{2-[2-(5-fluoro-1H-indol-3-yl)ethylamino]ethoxy}benzofuran-2-carboxylic acid amide Synthesis scheme:

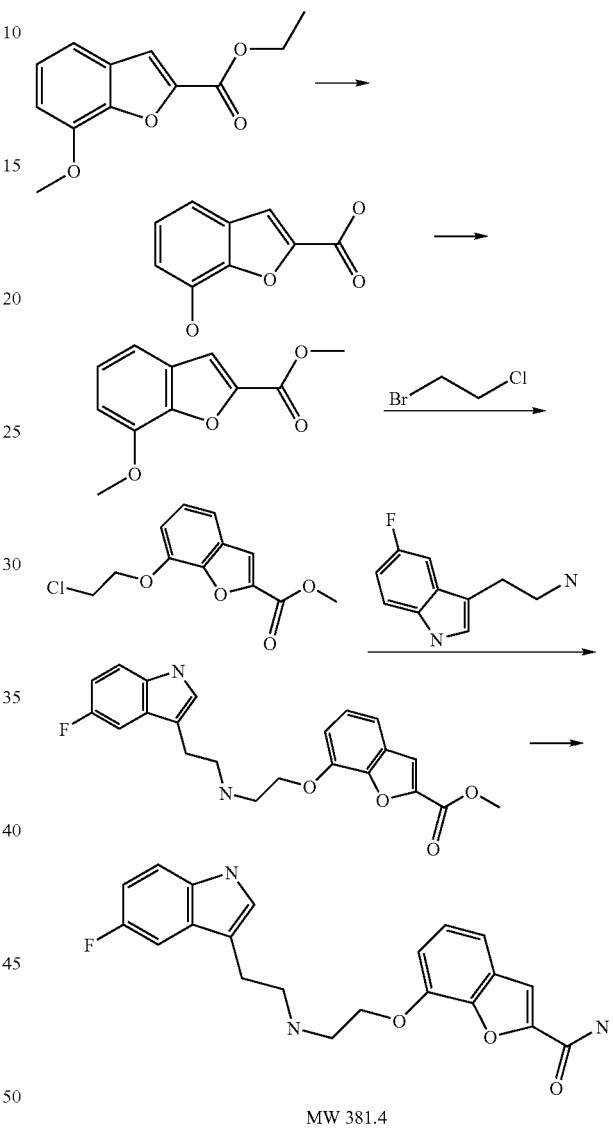

MW 381.4

Preparation of 7-hydroxybenzofuran-2-carboxylic acid ethyl ester 2 g of 7-methoxybenzofuran-2-carboxylic acid ethyl ester are dissolved in 50 ml of dichloromethane. The solution is cooled to −15° C., and 8.5 ml of boron tribromide are added under N$_2$. The reaction mixture is stirred for about 3 h at this temperature and overnight at room temperature. 10 ml of methanol and 20 ml of NaCl solution are added, and the mixture is extracted with ethyl acetate.

The organic phases are combined, dried and evaporated. The residue is triturated with petroleum ether, filtered off and dried, giving 1.87 g of 7-hydroxybenzofuran-2-carboxylic acid.

The carboxylic acid is dissolved in 30 ml of ethanol and cooled to about 0° C. 1.5 ml of thionyl chloride are slowly added dropwise, and the mixture is left to stir overnight at room temperature.

Water is added to the solution, during which the desired product precipitates, giving 1.5 g of 7-hydroxybenzofuran-2-carboxylic acid ethyl ester.

EI-MS (M)+ 205

In the same way, 7-hydroxybenzofuran-2-carboxylic acid methyl ester is obtained if methanol is used instead of ethanol.

EI-MS (M)+ 192

Preparation of
7-(2-chloroethoxy)benzofuran-2-carboxylic acid methyl ester 2.8 g of the previously obtained 7-hydroxybenzofuran-2-carboxylic acid methyl ester and 5.2 ml of 1-bromo-2-chloroethane are dissolved in 60 ml of acetone, and 2 g of potassium carbonate and 20 mg of potassium iodide are added. The entire mixture is boiled under reflux for two days.

For work-up, the solvent is stripped off in a Rotavapor. Water is added to the residue, which is then extracted with ethyl acetate. The entire organic phases are dried using anhydrous sodium sulfate, filtered, and the solvent is stripped off in a Rotavapor, giving 2.8 g of the desired substance.

HPLC-MS (M+H)+ 255

Preparation of 7-{2-[2-(5-fluoro-1H-indol-3-yl)ethylamino]ethoxy}benzofuran-2-carboxylic acid amide 318 mg of the material prepared above and 215 mg of 2-(5-fluoro-1H-indol-3-yl)ethylamine are dissolved in 10 ml of acetonitrile. 415 mg of potassium carbonate and 83 mg of potassium iodide are added. The mixture is left to boil under reflux for about 3 days.

For work-up, the reaction mixture is added to water/ice. The mixture is extracted with ethyl acetate. The entire organic phases are dried using anhydrous sodium sulfate, filtered, and the solvent is stripped off in a Rotavapor.

For purification, a flash silica-gel chromatography is carried out (dichloromethane/methanol 9/1).

80 mg of 7-{2-[2-(5-fluoro-1H-indol-3-yl)ethylamino]ethoxy}benzofuran-2-carboxylic acid ethyl ester are isolated.

HPLC-ESI-MS (M+H)+ 397

The ester is dissolved in 2 ml of methanol, and 4 ml of 25% ammonia solution are added. The entire mixture is stirred overnight at room temperature. For purification, a preparative HPLC is carried out:

| | |
|---|---|
| Column: | RP 18 (7 mum) Lichrosorb 250 × 25 (Art. No. 151494) |
| Eluent: | A = 98 H$_2$O, 2 CH$_3$CN + 0.1% of TFA |
| | B = 10 H$_2$O, 90 CH$_3$CN + 0.1% of TFA |
| UV: 225 NM; | |
| Flow rate: 10 ml/min (1 fraction = 1 minute) | |

| | | |
|---|---|---|
| Gradient: | 0 min | 15% of B |
| | 5 min | 15% of B |
| | 50 min | 80% of B |
| | 70 min | 95% |

23 mg of the desired substance are obtained.

HPLC-ESI-MS (M+H)+ 382 b) All the following products are obtained analogously to the example synthesis by the synthesis scheme indicated above and the working procedures.

| EXAMPLES | MW | SALT | MW SALT | NAME |
|---|---|---|---|---|
| 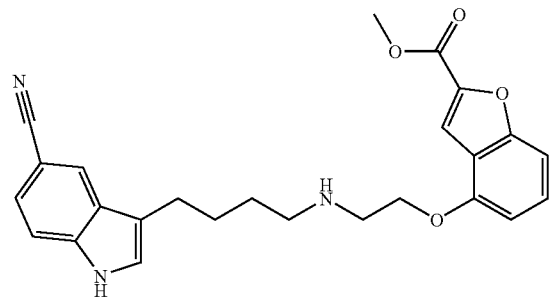  Example 2 | 431.5 | trifluoroacetate | 545.5 | 4-{2-[4-(5-Cyano-1H-indol-3-yl)-butylamino]ethoxy}-benzofuran-2-carboxylic acid methyl ester |
| 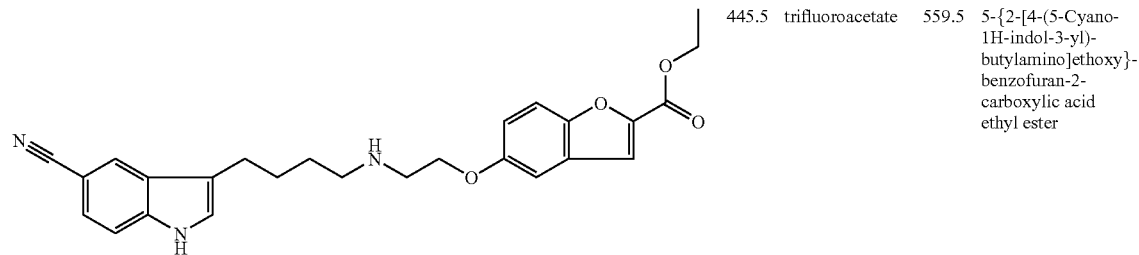  Example 3 | 445.5 | trifluoroacetate | 559.5 | 5-{2-[4-(5-Cyano-1H-indol-3-yl)-butylamino]ethoxy}-benzofuran-2-carboxylic acid ethyl ester |

-continued

| EXAMPLES | MW | SALT | MW SALT | NAME |
|---|---|---|---|---|
| Example 4 | 445.5 | trifluoroacetate | 559.5 | 6-{2-[4-(5-Cyano-1H-indol-3-yl)-butylamino]ethoxy}-benzofuran-2-carboxylic acid ethyl ester |
| Example 5 | 416.5 | bis-trifluoroacetate | 644.5 | 4-{2-[4-(5-Cyano-1H-indol-3-yl)-butylamino]ethoxy}-benzofuran-2-carboxylic acid amide |
| Example 6 | 445.5 | trifluoroacetate | 559.5 | 7-{2-[4-(5-Cyano-1H-indol-3-yl)butylamino]ethoxy}benzofuran-2-carboxylic acid ethyl ester |
| Example 7 | 431.5 | | | 7-{2-[4-(5-Cyano-1H-indol-3-yl)butylamino]ethoxy}benzofuran-2-carboxylic acid methyl ester |

-continued

| EXAMPLES | MW | SALT | MW SALT | NAME |
|---|---|---|---|---|
| 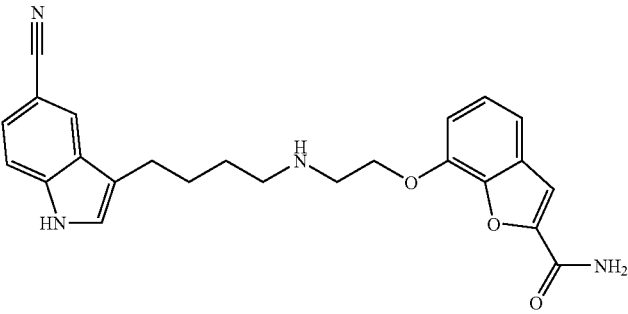Example 8 | 416.5 | | | 7-{2-[4-(5-Cyano-1H-indol-3-yl)butylamino]-ethoxy}benzofuran-2-carboxylic acid amide |
| 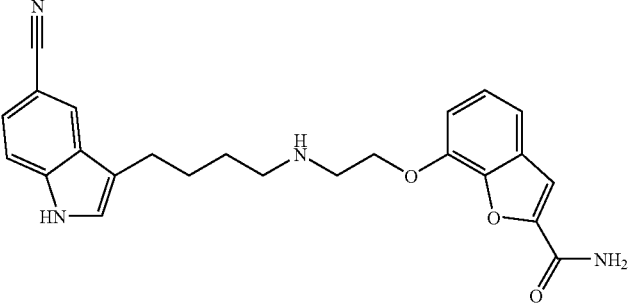Example 9 | 416.5 | bis-trifluoroacetate | 644.5 | 7-{2-[4-(5-Cyano-1H-indol-3-yl)butylamino]-ethoxy}benzofuran-2-carboxylic acid amide |
| 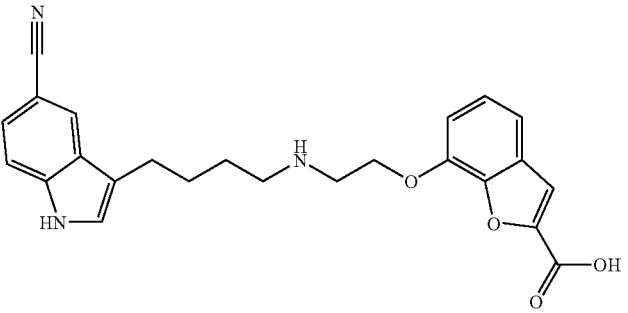Example 10 | 417.5 | | | 7-{2-[4-(5-Cyano-1H-indol-3-yl)butylamino]-ethoxy}benzofuran-2-carboxylic acid |
| 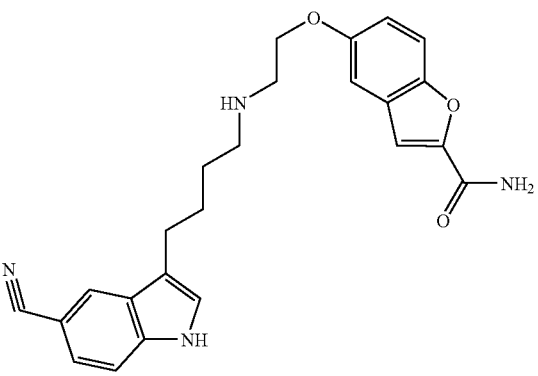Example 11 | 416.5 | | | 5-{2-[4-(5-Cyano-1H-indol-3-yl)butylamino]-ethoxy}benzofuran-2-carboxylic acid amide |

-continued

| EXAMPLES | MW | SALT | MW SALT | NAME |
|---|---|---|---|---|
| Example 12 | 381.4 | trifluoroacetate | 495.4 | 5-{2-[2-(5-Fluoro-1H-indol-3-yl)ethylamino]-ethoxy}benzofuran-2-carboxylic acid amide |
| Example 13 | 416.5 | | | 6-{2-[4-(5-Cyano-1H-indol-3-yl)butylamino]-ethoxy}benzofuran-2-carboxylic acid amide |
| Example 14 | 510.4 | | | 5-Bromo-7-{2-[4-(5-cyano-1H-indol-3-yl)-butylamino]ethoxy}-benzofuran-2-carboxylic acid methyl ester |
| Example 15 | 495.4 | | | 5-Bromo-7-{2-[4-(5-cyano-1H-indol-3-yl)-butylamino]ethoxy}-benzofuran-2-carboxylic acid amide |

-continued

| EXAMPLES | MW | SALT | MW SALT | NAME |
|---|---|---|---|---|
| Example 16 | 461.5 | | | 7-{2-[4-(5-Cyano-1H-indol-3-yl)butylamino]-ethoxy}-5-nitro-benzo-furan-2-carboxylic acid amide |
| Example 17 | 388.4 | bis-trifluoroacetate | 616.5 | 7-{2-[2-(5-Cyano-1H-indol-3-yl)ethylamino]-ethoxy}benzofuran-2-carboxylic acid amide |
| Example 18 | 402.5 | | | 7-{3-[2-(5-Cyano-1H-indol-3-yl)ethylamino]-propoxy}benzofuran-2-carboxylic acid amide |
| Example 19 | 395.4 | bis-trifluoroacetate | 623.5 | 7-{3-[2-(5-Fluoro-1H-indol-3-yl)ethylamino]-propoxy}benzofuran-2-carboxylic acid amide |

Characterisation of the above-mentioned examples:

| Example | MW | MS result |
|---|---|---|
| 2 | 431.5 | MALDI-MS(M + H)$^+$ 432 |
| 3 | 445.5 | MALDI-MS(M + H)$^+$ 446 |
| 4 | 445.5 | EI-MS(M)$^+$ 445 |
| 5 | 416.5 | HPLC-ESI-MS(M + H)$^+$ 417 |
| 6 | 445.5 | HPLC-ESI-MS(M + H)$^+$ 446 |
| 7 | 431.5 | HPLC-ESI-MS(M + H)$^+$ 432 |
| 8 | 416.5 | EI-MS(M)$^+$ 416 |
| 9 | 416.5 | EI-MS(M)$^+$ 416 |
| 10 | 417.5 | HPLC-ESI-MS(M + H)$^+$ 418 |
| 11 | 416.5 | HPLC-ESI-MS(M + H)$^+$ 417 |
| 12 | 381.4 | HPLC-ESI-MS(M + H)$^+$ 382 |
| 13 | 416.5 | HPLC-ESI-MS(M + H)$^+$ 417 |
| 14 | 510.4 | EI-MS(M)$^+$ 510 |
| 15 | 495.4 | EI-MS(M)$^+$ 495 |
| 16 | 461.5 | EI-MS(M)$^+$ 461 |
| 17 | 388.4 | HPLC-MS(M + H)$^+$ 389 |
| 18 | 402.5 | HPLC-ESI-MS(M + H)$^+$ 403 |
| 19 | 395.4 | HPLC-MS(M + H)$^+$ 396 |

EI-MS: electron impact mass spectroscopy
ESI-MS: electrospray mass spectroscopy
MALDI-MS: matrix assisted laser desorption/ionisation mass spectroscopy The examples below relate to pharmaceutical compositions

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I is melted with 100 g of soya lecithin and 1400 g of cocoa butter, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2\ H_2O$, 28.48 g of $Na_2HPO_4 \cdot 12\ H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

EXAMPLE I

Inhalation spray 14 g of active ingredient of the formula I are dissolved in 10 l of isotonic NaCl solution, and the solution is transferred into commercially available spray containers with a pump mechanism. The solution can be sprayed into the mouth or nose. One spray shot (about 0.1 ml) corresponds to a dose of about 0.14 mg.

The invention claimed is:
1. A compound of formula I

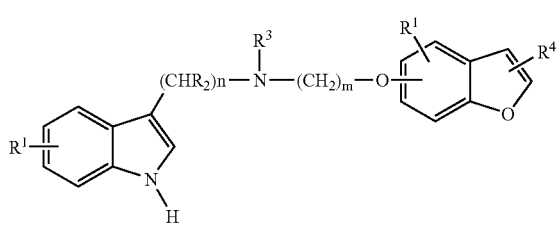

in which
R$^1$ denotes mono- or disubstitution by OH, OA, CN, Hal, COR or CH$_2$R,
R denotes OH, OA, NH$_2$, NHA or NA$_2$,
R$^2$, R$^3$ denote H or A,
R$^4$ denotes H, mono- or disubstitution by OH, OA, NH$_2$, NHA, NA$_2$, CN, Hal, COR or CH$_2$R, A denotes alkyl having 1, 2, 3, 4, 5 or 6 atoms,
Hal denotes F, Cl, Br or I,
m denotes 2, 3, 4, 5 or 6, and
n denotes 1, 2, 3 or 4,
or a pharmaceutically acceptable derivative, solvate or stereoisomer thereof.

2. A compound according to claim 1, in which $R^1$ denotes CN or F, and R denotes $NH_2$, OH, O-methyl or O-ethyl.

3. A compound according to claim 1, in which $R^2$ denotes H or methyl, and $R^3$ denotes H or methyl.

4. A compound according to claim 1, in which A denotes methyl or ethyl.

5. A compound according to claim 1, in which $R^4$ denotes $CONH_2$, $COOC_2H_5$ or CONHA.

6. A compound according to claim 1, in which m denotes 2 or 3, and n denotes 2 or 4.

7. A compound according to claim 1, which is
4-{2-[4-(5-cyano-1H-indol-3-yl)butylamino]ethoxy}benzofuran-2-carboxylic acid methyl ester,
5-{2-[4-(5-cyano-1H-indol-3-yl)butylamino]ethoxy}benzofuran-2-carboxylic acid ethyl ester,
6-{2-[4-(5-cyano-1H-indol-3-yl)butylamino]ethoxy}benzofuran-2-carboxylic acid ethyl ester,
4-{2-[4-(5-cyano-1H-indol-3-yl)butylamino]ethoxy}benzofuran-2-carboxylic acid amide,
7-{2-[4-(5-cyano-1H-indol-3-yl)butylamino]ethoxy}benzofuran-2-carboxylic acid ethyl ester,
7-{2-[4-(5-cyano-1H-indol-3-yl)butylamino]ethoxy}benzofuran-2-carboxylic acid methyl ester,
7-{2-[4-(5-cyano-1H-indol-3-yl)butylamino]ethoxy}benzofuran-2-carboxylic acid amide,
7-{2-[4-(5-cyano-1H-indol-3-yl)butylamino]ethoxy}benzofuran-2-carboxylic acid,
5-{2-[4-(5-cyano-1H-indol-3-yl)butylamino]ethoxy}benzofuran-2-carboxylic acid amide,
5-{2-[2-(5-fluoro-1H-indol-3-yl)ethylamino]ethoxy}benzofuran-2-carboxylic acid amide,
6-{2-[4-(5-cyano-1H-indol-3-yl)butylamino]ethoxy}benzofuran-2-carboxylic acid amide,
5-bromo-7-{2-[4-(5-cyano-1H-indol-3-yl)butylamino]ethoxy}benzofuran-2-carboxylic acid methyl ester,
5-bromo-7-{2-[4-(5-cyano-1H-indol-3-yl)butylamino]ethoxy}benzofuran-2-carboxylic acid amide,
7-{2-[2-(5-fluoro-1H-indol-3-yl)ethylamino]ethoxy}benzofuran-2-carboxylic acid amide,
7-{2-[4-(5-cyano-1H-indol-3-yl)butylamino]ethoxy}-5-nitrobenzofuran-2-carboxylic acid amide,
7-{2-[2-(5-cyano-1H-indol-3-yl)ethylamino]ethoxy}benzofuran-2-carboxylic acid amide,
7-{3-[2-(5-cyano-1H-indol-3-yl)ethylamino]propoxy}benzofuran-2-carboxylic acid amide, or
7-{3-[2-(5-fluoro-1H-indol-3-yl)ethylamino]propoxy}benzofuran-2-carboxylic acid amide.

8. A process for preparing a compound of formula I according to claim 1, comprising reacting a compound of formula II <chemical structure, formula II: Hal—(CH₂)ₘ—O— attached to benzofuran with R¹ and R⁴ substituents> in which
$R^1$, $R^4$, Hal and m have the meanings indicated for the compound of formula I, with a compound of formula III <chemical structure, formula III: indole with R¹ substituent and (CHR²)ₙ—NHR³ side chain> in which
$R^1$, $R^2$ $R^3$ and n have the meanings indicated for the compound of formula I,
and optionally a basic or acidic compound of formula I is converted into one of its salts or solvates by treatment with an acid or base.

9. A pharmaceutical composition, comprising a compound according to claim 1 and a pharmaceutically acceptable carrier.

10. A compound according to claim 1, wherein the pharmaceutically acceptable derivative of a compound of formula I is a pharmaceutically acceptable salt of a compound of formula I.

11. A compound according to claim 1, which is an isolated stereoisomer of a compound of formula I.

12. A compound according to claim 1, which is a basic or acidic compound of formula I.

13. A pharmaceutical composition, comprising a compound according to claim 7 and a pharmaceutically acceptable carrier.

* * * * *